(12) United States Patent
Derk et al.

(10) Patent No.: US 11,129,638 B2
(45) Date of Patent: Sep. 28, 2021

(54) MANUAL DEBRIDEMENT IMPLEMENT

(71) Applicants: Francis F. Derk, San Antonio, TX (US); Derek T. Denton, Fair Oaks Ranch, TX (US)

(72) Inventors: Francis F. Derk, San Antonio, TX (US); Derek T. Denton, Fair Oaks Ranch, TX (US)

(73) Assignee: MDM Wound Ventures, Inc., San Antonio, TX (US)

( * ) Notice: Subject to any disclaimer, the term of this patent is extended or adjusted under 35 U.S.C. 154(b) by 635 days.

(21) Appl. No.: 15/414,715

(22) Filed: Jan. 25, 2017

(65) Prior Publication Data

US 2017/0215906 A1 Aug. 3, 2017

Related U.S. Application Data

(60) Provisional application No. 62/290,623, filed on Feb. 3, 2016.

(51) Int. Cl.
| | |
|---|---|
| *A61B 17/32* | (2006.01) |
| *A61B 17/54* | (2006.01) |
| A61B 50/30 | (2016.01) |
| A61B 17/00 | (2006.01) |

(52) U.S. Cl.
CPC ............ *A61B 17/32* (2013.01); *A61B 17/54* (2013.01); *A61B 50/30* (2016.02); *A61B 2017/00761* (2013.01); *A61B 2017/320004* (2013.01); *A61B 2017/320008* (2013.01)

(58) Field of Classification Search
CPC .................... A61B 50/30; A61B 17/32; A61B 2017/00761; A61B 17/54; A61B 17/52; A61B 17/50; A61B 2017/320004; A45D 26/0004; A45D 2200/1054
USPC .......................................... 606/131
See application file for complete search history.

(56) References Cited

U.S. PATENT DOCUMENTS

| | | | |
|---|---|---|---|
| D617,498 S * | 6/2010 | Martin .................. | D24/147 |
| D741,017 S * | 10/2015 | Exley ..................... | D28/59 |
| 2007/0208354 A1* | 9/2007 | Barraclough .......... | A45D 26/00 606/133 |
| 2008/0091216 A1* | 4/2008 | Grace ................... | A61B 17/54 606/131 |

(Continued)

*Primary Examiner* — Darwin P Erezo
*Assistant Examiner* — Brigid K Byrd
(74) *Attorney, Agent, or Firm* — The Law Offices of John G. Posa

(57) ABSTRACT

An inexpensive yet effective implement for manual debridement comprises an elongated, integrally molded hand-held member having a proximal handle with a gripping portion, a distal head portion, and a flex portion between the handle and head portions. The head portion defines a bottom surface with a plurality of fluted structures, each fluted structure featuring a sharp edge. The handle portion is angled relative to the bottom surface of the head portion. The implement is packaged in sterilized form and intended to be disposed after use. In the preferred embodiment the fluted structures define partial, truncated cones, such that sharp edge is a curve or semi-circle. The gripping portion may also include a ruler or graduated markings. The flex portion may be ribbed or accordion-shaped to enhance flexing. The proximal-most portion of the handle includes a downward curve to maintain a user's grip.

8 Claims, 2 Drawing Sheets

(56) References Cited

U.S. PATENT DOCUMENTS

| | | | |
|---|---|---|---|
| 2010/0145359 A1* | 6/2010 | Keller | A61B 17/54 |
| | | | 606/131 |
| 2010/0228267 A1* | 9/2010 | Mercado | A61B 5/1076 |
| | | | 606/131 |
| 2011/0282337 A1* | 11/2011 | Hall | A61B 10/0266 |
| | | | 606/33 |
| 2012/0085850 A1* | 4/2012 | Tetreault | A47J 43/25 |
| | | | 241/101.2 |
| 2013/0138119 A1* | 5/2013 | Luzon | A61B 17/54 |
| | | | 606/131 |

* cited by examiner

MANUAL DEBRIDEMENT IMPLEMENT

REFERENCE TO RELATED APPLICATIONS

This application claims priority to U.S. Provisional Patent Application Ser. No. 62/290,623, Filed Feb. 3, 2016, the entire content of which is incorporated herein by reference.

FIELD OF THE INVENTION

This invention relates generally to debridement and, in particular, to an inexpensive, disposable yet effective tool for removal of dead, damaged, or infected tissue

BACKGROUND OF THE INVENTION

Debridement relates to the medical removal of dead, damaged, or infected tissue to improve the healing potential of the remaining healthy tissue. Removal may be surgical, mechanical, chemical, autolytic (self-digestion), and by maggot therapy, where certain species of live maggots selectively eat only the necrotic tissue. In oral hygiene and dentistry, debridement refers to the removal of plaque and calculus that have accumulated on the teeth. Podiatry practitioners remove conditions such as calluses and verrucas. Debridement is an important part of the healing process for burns and other serious wounds.

There are many hand-held debridement tools, many of which require power for cutting or other operations. As one example, Published U.S. Patent Application No. 2012/0101512 describes tools for aiding a user in debriding necrotic tissue. One such tool includes a motor connected to a power source and a blade is coupled to a first end of the housing. The blade is operable to vibrate when the motor is powered. This debridement tool further includes a lighting element disposed within the housing and beneath a cutting edge of the blade to illuminate the tissue site. In some embodiments, the lighting element operates at a particular wavelength that assists in distinguishing between necrotic tissue and healthy tissue.

Non-powered wound debridement instruments include the one described in U.S. Pat. No. 8,679,133, intended for treatment of chronic wounds. The tool has an elongate handle with a distal end, a proximal end, and a middle section. An elongate tubular blade body extends distally from the handle distal end and terminates at a distal cutting edge. The tubular body defines a cavity and has a longitudinal axis. The distal cutting edge follows the arc of the tubular body and is angled relative to the longitudinal axis. In some embodiments the tubular body is an incomplete tube, having a longitudinally-extending gap formed therein. Some embodiments may also have a scraping element extending proximally from the handle proximal end.

While existing powered and non-powered debridement devices are no doubt effective to some degree, they tend to be somewhat complicated and expensive. The need remains for an economical yet effective alternative.

SUMMARY OF THE INVENTION

This invention resides in an inexpensive yet effective implement for manual debridement procedures. The preferred embodiment comprises an elongated, integrally molded hand-held member having a proximal handle with a gripping portion, a distal head portion, and a flex portion between the handle and head portions. The head portion defines a bottom surface with a plurality of fluted structures, each fluted structure featuring a sharp edge. The handle portion is angled relative to the bottom surface of the head portion. The implement is packaged in sterilized form and intended to be disposed after use.

In the preferred embodiment the fluted structures define partial, truncated cones, such that sharp edge is a curve or semi-circle. The handle portion may further include a bulbous portion between the gripping portion and the flex portion to function as a thumb or finger rest. The gripping portion may also include a ruler or graduated markings. The flex portion may be ribbed or accordion-shaped to enhance flexing. The proximal-most portion of the handle includes a downward curve to maintain a user's grip.

DETAILED DESCRIPTION OF THE INVENTION

Figure 3:
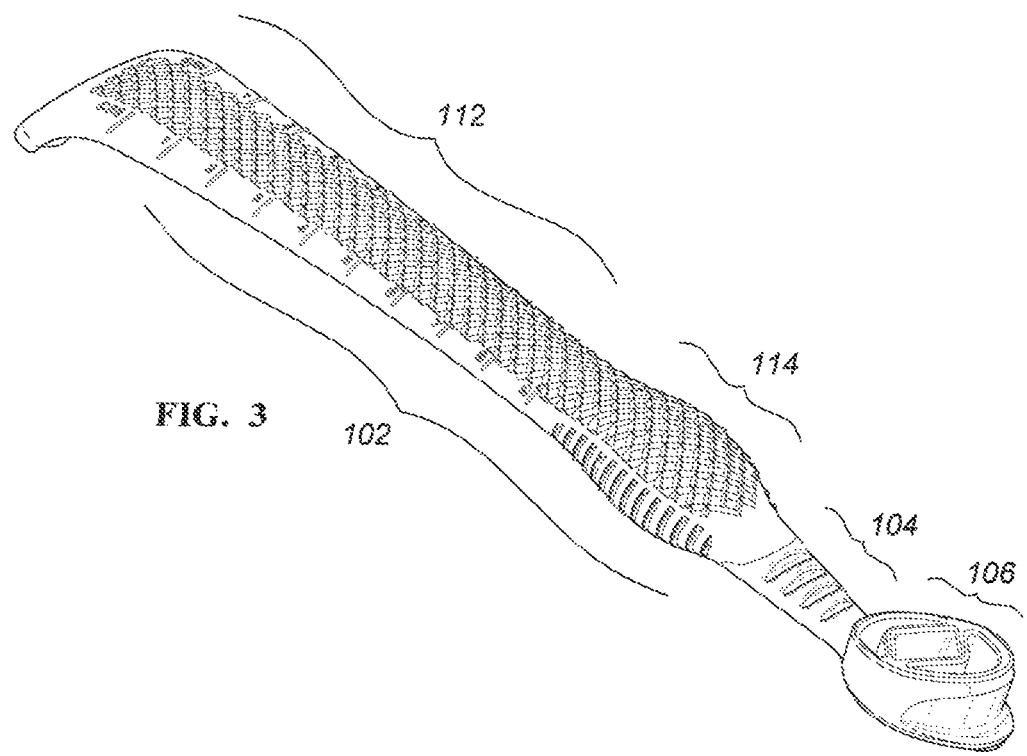
FIG. 3 is an oblique view of the preferred embodiment.
Figure 2:
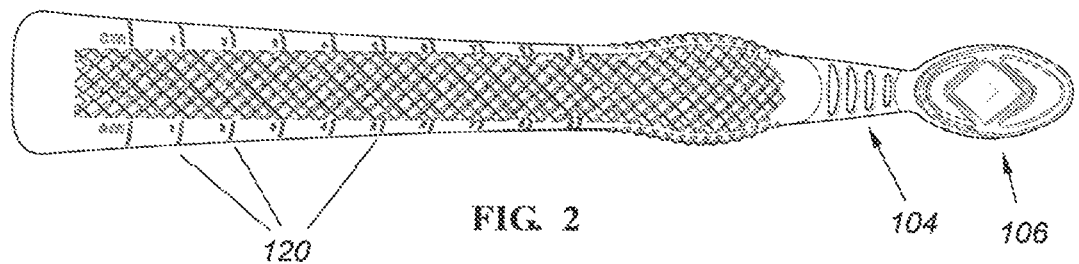
FIG. 2 is a top view of the preferred embodiment.
Figure 1:
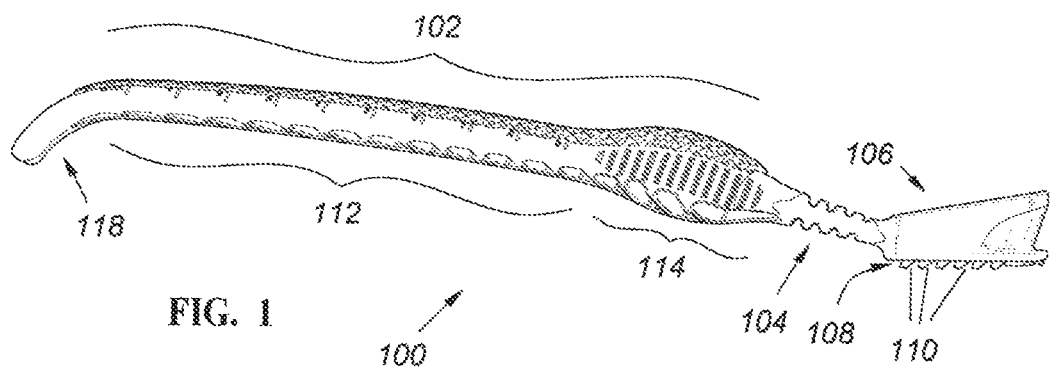
FIG. 1 is a side view of the preferred embodiment of the invention.
Figure 4:
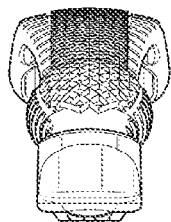
FIG. 4 is a front view.
Figure 5:
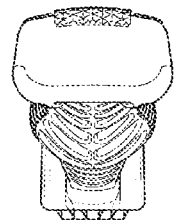
FIG. 5 is a back view.
Figure 6:
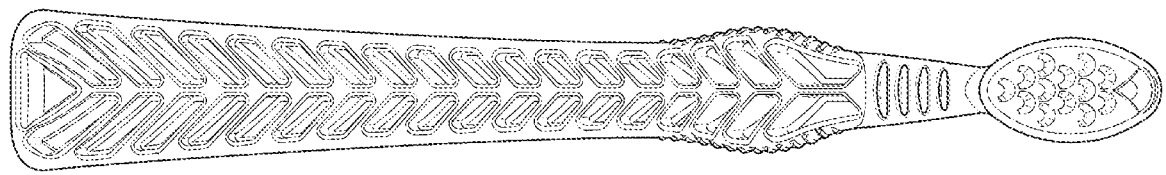
FIG. 6 is a bottom view.

The accompanying Figures present different views of the preferred embodiment of the invention, which resides in a handheld tool 100 having a proximal handle portion 102, a head portion 106 and a flex portion 104 between the handle and head portions. As perhaps best seen in FIG. 1, the flex portion 106 has an accordion shape when viewed form the side, enabling the handle to flex relative to the head while performing a debridement procedure.

In terms of dimensions, the length of the implement is between about 6 and 12 inches, more preferably between 7 and 10 inches, and even more preferably between 8 and nine inches. The width of the implement is between ½ to 1-½ inches, with a preferred width of around 1 inch or greater.

The head portion has a bottom flat surface 108 with a plurality of sharp flutes 110 described in further below. With the fluted surface oriented horizontally, the handle and flex portions of the implement define an angle in the range of 5 to 35 degrees, more preferably in the range of 10 to 20 degrees.

The handle portion includes a gripping portion 112 and a bulbous portion 114 between the gripping portion and the flex portion 104. While optional, the bulbous portion functions as a thumb rest to assist in applying forward pressure during the debridement process. In the preferred embodiment, both the top and bottom surfaces of both the gripping and bulbous portions include textured surfaces as shown in the Figures. The sides of the bulbous portion may also feature side ribs to further improve gripping. As a further desirable option, the proximal-most end of the handle may include a downward curve at 118 to prevent a user's hand from sliding off the back of the implement.

The implement is preferably constructed as a unitary object, fabricated though injection molding, for example, to reduce cost. Any number of plastics may be used for construction, including PCV, polyethylene and vinyl, though polypropylene is preferably used to achieve low cost and desired properties. One such desired property is a tradeoff between appropriate stiffness for effective scraping and flexibility in the flex portion for desired contact with tissue, bone or wound surfaces. In the preferred embodiment the implement 100 is packaged in a sterile condition to be opened before or during a procedure and discarded after use as a disposable item.

Figure 7:
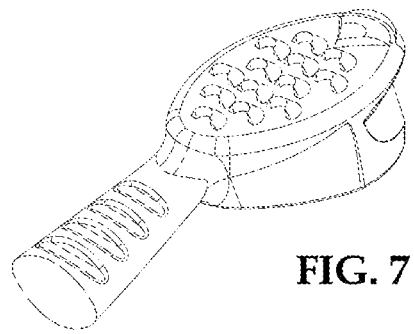
FIG. 7 is an oblique view of the fluted head of the implement seen from a first perspective.
Figure 8:
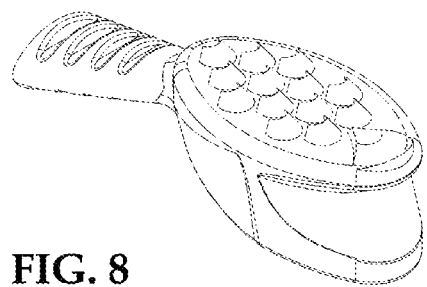
FIG. 8 is an oblique view of the fluted head of the implement seen from a different perspective.
Figure 9:
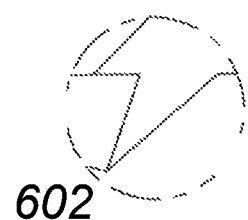
FIG. 9 is a cross section of one of the flutes taken through a centerline thereof.

FIGS. 7, 8 are oblique view of the fluted head of the implement seen from different perspectives, and FIG. 9 is a cross-sectional view through one of the flutes from proximal to distal. As can be seen, the flute has a sharp point 602 oriented toward the handle of the implement, enabling the user to pull the implement toward them during debridement. The flutes themselves are preferably partial scallops, with an inner cylindrical or conical surface that intersects with an outer conical surface, thereby forming a sharp circular or otherwise curved edge. These sharp edges all preferably lie in a plane parallel to the bottom surface from which the flutes extend. The proximal end of the fluted bottom of the head may include a raised, V-shaped body to assist in diverting debrided tissue.

The gripping portion 112 of the implement may optionally include labeled rulings 120, enabling the handle to be used for width and/or depth measurements for procedural recording activities. Such rulings are again integrally molded into the implement.

The invention claimed is:

1. A wound debridement implement, comprising:
    an elongated, integrally molded hand-held member having a proximal handle with a gripping portion, a distal head portion, and a flex portion between the handle and head portions;
    the head portion defining a bottom surface with a plurality of fluted structures, each fluted structure defining a partial, truncated cone with a curving or semi-circular sharp edge oriented toward the handle of the implement such that a user pulls the implement toward them during debridement;
    the handle portion being angled relative to the bottom surface of the head portion; and
    wherein the implement is packaged in sterilized form and disposable after use.

2. The implement of claim 1, wherein the handle portion further includes a bulbous portion between the gripping portion and the flex portion.

3. The implement of claim 1, wherein the flex portion is ribbed or accordion-shaped to enhance flexing.

4. The implement of claim 1, wherein the proximal-most portion of the handle includes a downward curve to maintain a user's grip.

5. The implement of claim 1, wherein the integrally molded member is composed of polypropylene.

6. The implement of claim 1, wherein the gripping portion includes a ruler or graduated markings.

7. The implement of claim 1, wherein the fluted structures are partial scallops, having an inner cylindrical or conical surface that intersects with an outer conical surface to form the curving or semi-circular sharp edge.

8. The implement of claim 1, wherein the sharp edges all lie in a plane parallel to the bottom surface from which the fluted structures extend.

\* \* \* \* \*